(12) United States Patent
Chan et al.

(10) Patent No.: US 8,301,258 B2
(45) Date of Patent: Oct. 30, 2012

(54) METHODS AND DEVICES FOR PREVENTING ANKLE SPRAIN INJURIES

(75) Inventors: Kai-Ming Chan, Hong Kong (CN); Tik Pui Daniel Fong, Hong Kong (CN); Shu Hang Patrick Yung, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 78 days.

(21) Appl. No.: 12/539,265

(22) Filed: Aug. 11, 2009

(65) Prior Publication Data

US 2010/0042182 A1   Feb. 18, 2010

Related U.S. Application Data

(60) Provisional application No. 61/088,949, filed on Aug. 14, 2008.

(51) Int. Cl.
*A61N 1/00* (2006.01)
(52) U.S. Cl. .................. 607/48; 607/51; 607/52
(58) Field of Classification Search .......... 607/48, 607/51–52; 128/892
See application file for complete search history.

(56) References Cited

U.S. PATENT DOCUMENTS

| | | | |
|---|---|---|---|
| 2003/0060740 A1 | 3/2003 | Faghri | |
| 2004/0088025 A1* | 5/2004 | Gesotti | ............ 607/49 |
| 2004/0173220 A1* | 9/2004 | Harry et al. | ............ 128/892 |
| 2005/0192645 A1 | 9/2005 | Stein et al. | |
| 2007/0146189 A1* | 6/2007 | Wesselink et al. | ............ 341/155 |
| 2007/0225769 A1 | 9/2007 | Smith et al. | |

FOREIGN PATENT DOCUMENTS

| | | |
|---|---|---|
| CN | 1802140 A | 7/2006 |
| CN | 1956692 A | 5/2007 |
| WO | 2005016144 A1 | 2/2005 |

OTHER PUBLICATIONS

Chan, et al., A mechanical supination sprain simulator for studying ankle supination sprain kinematics. *Journal of Biomechanics* 41 (2008) p. 2571 2574.
Fong, et al., Biomechanics of Supination Ankle Sprain—A Case Report of an Accidental Injury Event in the Laboratory. *The American Journal of Sports Medicine*, vol. 37, No. 4, p. 822-827 (2009).
International Search Report issued in corresponding PCT Application No. PCT/CN2009/073217, dated Oct. 22, 2009.

* cited by examiner

*Primary Examiner* — Nicole F Lavert
(74) *Attorney, Agent, or Firm* — Knobbe Martens Olson & Bear LLP

(57) ABSTRACT

Devices and methods for preventing ankle sprain injuries. To protect the ankle joint from acute ankle supination or inversion sprain injuries, the device comprises a sensing part configured to sense data of an ankle motion; an analyzing part configured to analyze the data to judge whether the motion is a sprain motion; and a stimulating part configured to stimulate one or more lower limb muscles against the motion in light of a result of the analyzing. The method also involves sensing data of an ankle motion; analyzing the data to judge whether the motion is a sprain motion; and stimulating one or more lower limb muscles against the motion if the motion is a sprain motion.

22 Claims, 4 Drawing Sheets

METHODS AND DEVICES FOR PREVENTING ANKLE SPRAIN INJURIES

CROSS-REFERENCE TO RELATED APPLICATIONS

This application claims priority under 35 U.S.C. §119(e) to U.S. Provisional Application No. 61/088,949, filed on Aug. 14, 2008 (expired), the entire content of which is incorporated herein by reference.

BACKGROUND OF THE INVENTION

1. Field of the Invention

The present invention relates to a device and method for prevention of ankle sprain injuries. The device comprises a sensing part configured to sense data of an ankle motion; an analyzing part configured to analyze the data to judge whether the motion is a sprain motion; and a stimulating part configured to stimulate one or more lower limb muscles against the motion in view of the result of the analyzing component.

2. Description of the Related Art

Injuries to muscles, ligaments and bones in lower limbs, such as the lateral ankle ligaments, are very common in sports, which may cause pain and immobility of the legs or ankle joints. For example, injuries to ankle ligaments in the long term may lead to the development of ankle instability, which does not yet have an adequate treatment and rehabilitation protocol.

Most ankle sprain injuries are caused by a supination or inversion mechanism. It is known that the peroneal muscles are at the lateral aspect of the lower leg, which function to pronate or evert the ankle joint. Therefore, the peroneal muscles serve as the intrinsic defensive mechanism against ankle sprain injuries to resist excessive ankle supination or inversion. However, one of the etiologies of ankle sprain injuries is the slow reaction time of the peroneal muscles. Thus, in most of the injuries, the peroneal muscles are unable to catch up and react to provide the intrinsic protection.

Currently, myoelectric stimulation has been employed in various medical devices, such as "Functional Electric Stimulus" (FES), to initiate passive exercise to injured muscles for rehabilitation training. Moreover, similar technologies are employed in passive massage devices. In addition, similar techniques have been employed to assist walking in hemiplegic patients who cannot deliver neuromuscular activation to the leg muscle to walk. In all of these devices, electrical signals are delivered to the selected muscle group through pairs of electrodes, which replace the human intrinsic neuromuscular electrical stimulation. The electrical signals can trigger some biochemical changes in muscle cells, leading to contraction of the muscle and thus joint flexion or extension. However, these devices cannot provide quick reaction to prevent acute ankle sprain injuries.

SUMMARY OF THE INVENTION

To prevent an ankle sprain injury, an artificial trigger can be delivered to initiate a peroneal muscle function before the normal muscle reaction.

According to one aspect of the present invention, a device for preventing an ankle sprain injury is provided, which comprises a sensing part configured to sense data of an ankle motion; an analyzing part configured to analyze the data to judge whether the motion is a sprain motion; and a stimulating part configured to stimulate one or more lower limb muscles against the motion in light of a result of the analyzing.

According to another aspect of the present invention, a method for preventing an ankle sprain injury is provided, which comprises sensing data of an ankle motion; analyzing the data to judge whether the motion is a sprain motion; and stimulating one or more lower limb muscles against the motion if the motion is a sprain motion.

According to another aspect of the present invention, a shoe comprising the device described herein is provided.

DETAILED DESCRIPTION OF THE INVENTION

Hereinafter, a detailed description of embodiments of the present invention will be given with reference to the appended drawings.

Figure 1:
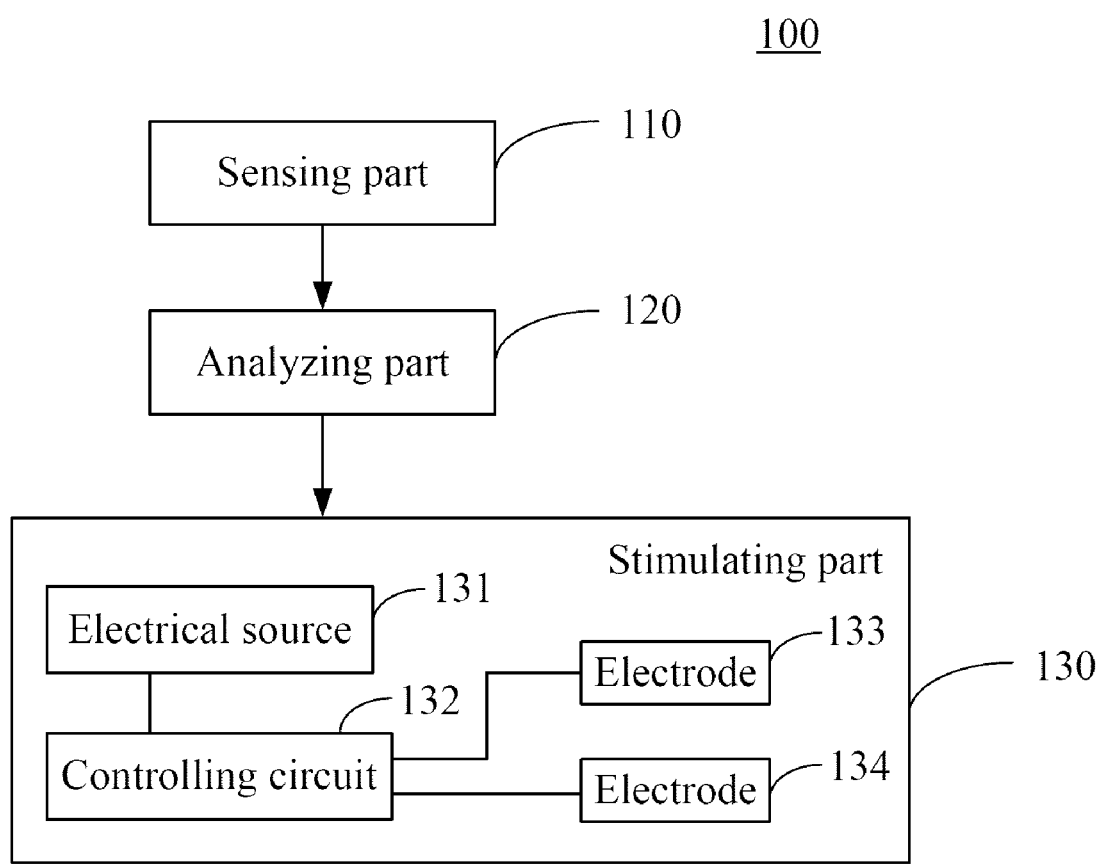
FIG. 1 shows a schematic block diagram of the device for preventing an ankle sprain injury according to an embodiment of the present invention.

Referring to FIG. 1, in one embodiment, a device 100 may include a sensing part 110, an analyzing part 120 and a stimulating part 130.

Figure 2:
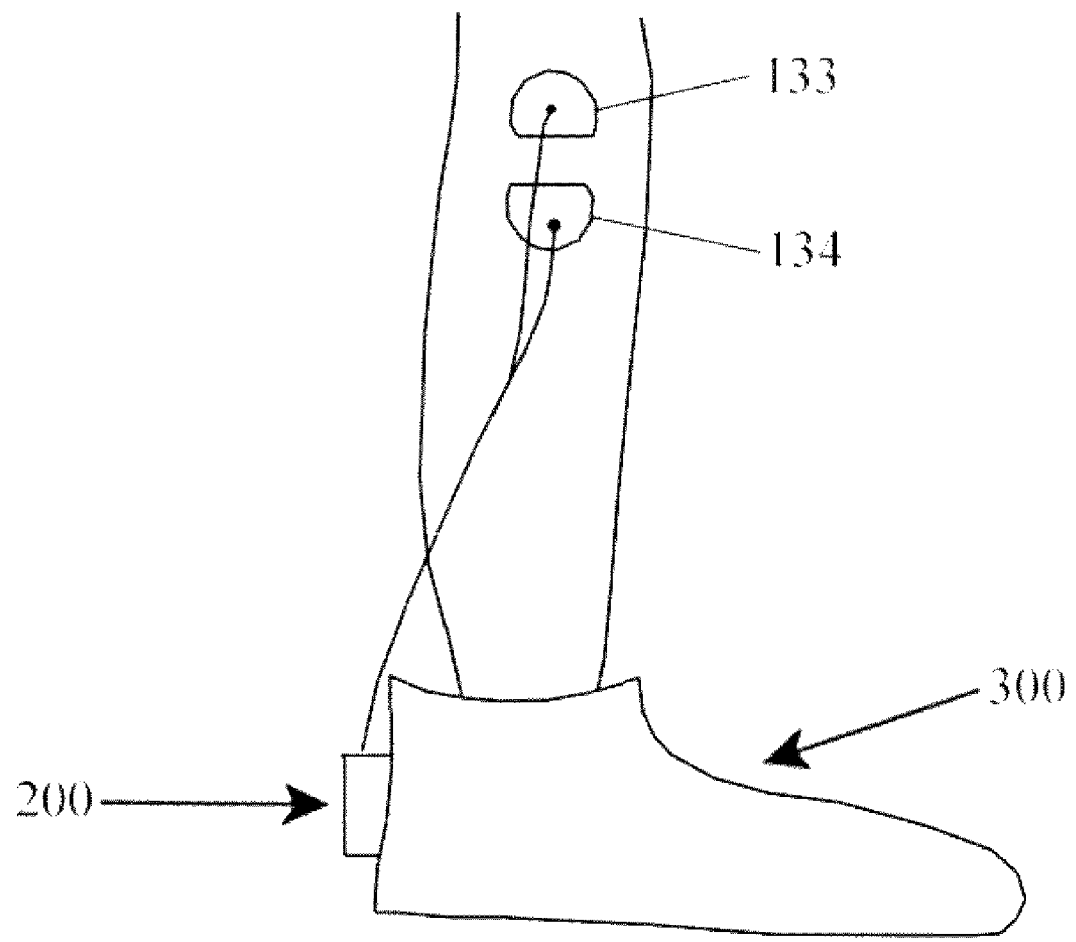
FIG. 2 shows a schematic view of a foot with the device according to an embodiment of the present invention.

The sensing part 110 is configured to sense the motions of a user's foot. To sense the motions of the foot, the sensing part 110 can be attached to an external or internal surface of a heel cup of a shoe, as shown in FIG. 2. Alternatively, the sensing part 110 also can be attached to a skin surface of a foot. In operation, the sensing part 110 senses and transmits the data of motions of the user's foot in a real-time manner. In an implementation, the sensing part 110 comprises a tri-axial accelerometer and a gyrometer for sensing the motions of the foot segment relative to the shank segment. In this case, the data to be sensed and transmitted is the ankle inversion velocity of the user's foot in motion. In the disclosure, the ankle inversion velocity means the rate of change of the ankle inversion degree of a foot. That is, $$\text{Ankle Inversion Velocity (deg/sec)} = \frac{\text{Ankle Inversion Degree (deg)}}{\text{Duration of Ankle Inversion (sec)}}$$

In another implementation, the sensing part 110 comprises a pressure sensor to sense the motions of the foot segment. In this case, the data to be sensed and transmitted by the sensing part 110 is the pressure to the user's foot in motion.

In other implementations, the sensing part 110 may comprise one or more selected from the group consisting of a tri-axial accelerometer, a gyrometer, a goniometer, a pressure sensor and the like.

According to one embodiment, the sampling frequency of the sensing part 110 may be adjustable. In another embodiment, the sampling frequency of the sensing part 110 is 50 Hz~1,000 Hz. For example, the sampling frequency of the sensing part 110 may be 100 Hz or 500 Hz.

The data for each of the motions sensed by the sensing part 110 are transmitted in real time to the analyzing part 120 through a wire or in a wireless manner. A threshold differentiating sprain motions from normal motions is preset in the analyzing part 120. Once data received about a motion exceed the threshold, the analyzing part 120 transmits a trigger signal to the stimulating part 130. Otherwise, no trigger signal will be sent out of the analyzing part 120 if the received data do not exceed the threshold, and the analyzing part 120 will process subsequent data.

In one embodiment, the threshold preset in the analyzing part 120 is adjustable for users with different weights or for different uses such as in walking, sporting, climbing, and so on.

The stimulating part 130 is provided for stimulating lower limb muscles to prevent ankle sprain injuries. According to one embodiment, the stimulating part 130 comprises an electrical source 131, a controlling circuit 132, and a pair of electrodes 133 and 134, as shown in FIG. 1. The electrical source 131 supplies electric power for the controlling circuit 132 connected with the electrodes 133 and 134.

In one embodiment, the sensing part 110, the analyzing part 120, the electrical source 131 and the controlling circuit 132 are encapsulated in a housing 200 attached to a heel cup of a shoe 300, and the electrodes 133 and 134 are attached to the skin surface of the peroneal muscle group so as to stimulate the peroneal muscle group, as shown in FIG. 2. It will be understood that the housing 200 also can be attached to any other position of a shoe according to the user's need in practice, by sewing, bonding or any other known coupling manner. Once the stimulating part 130 receives a trigger signal from the analyzing part 120, the controlling circuit 132 delivers an electric stimulation signal to the electrodes 133 and 134 so as to generate a pulse current through the peroneal muscle group in a lower limb of the user. In one embodiment, the electric stimulation signal is an electric potential difference in pulse with desired level.

When an electrical signal passes through the peroneal muscle group, the peroneal muscle group of the user may be stimulated to rapidly pronate or evert the ankle joint to prevent the ankle from an acute ankle sprain injury. In particular, when a pulse current from the controlling circuit 132 is delivered through the electrodes 133 and 134 to the peroneal muscle group, the peroneal muscle group may contract and initiate ankle pronation or eversion to resist the sudden supination or inversion.

According to one embodiment, the electrical signal from the controlling circuit 132 can be delivered through the muscle group within 20-30 ms after the start of a sprain injury. It is known that the torque latency of the ankle muscles is about 21-25ms. Therefore, the reaction time to a sprain injury is short enough and it could catch up to initiate peroneal muscle contraction to protect the ankle joint.

According to one embodiment, the electrical source 131 is a set of batteries. By using the electrical source 131, the controlling circuit 132 can output a pulse with a peak voltage of about 100-200V. Although the peak voltage is quite high, the current is small enough to ensure the safety for the user.

In another embodiment, the electrodes 133 and 134 are separated by a distance of 1-3 cm on the skin surface of the peroneal muscle group. Optionally, the electrodes 133 and 134 are disposable/replaceable skin-attached silver chloride discs. Furthermore, the electrodes 133 and 134 can be embedded in any accompanying brace or sock with a storage room at the lateral aspect of the lower leg. There may have accompanying apparel which should not block the direct contact of the electrodes 133 and 134 and the skin surface. For the safety, when none skin impedance is detected by the electrodes 133 and 134, the device 100 will not be activated.

Moreover, the controlling circuit 132 can comprise an on-off switch to control the delivery of the electrical signal to the electrode pair.

The physical variable to be sensed by the sensing part 110 and compared with the threshold may be any of variables characterizing the motions of a foot, such as the inversion angle, tilting angle (an angle of the foot segment relative to the ground), tilting velocity, and the like. In one embodiment, the ankle inversion velocity is the physical variable to be sensed. Then, the threshold differentiating sprain motions from normal motions is selected to be a bit higher than the range of the ankle inversion velocity of normal motions of a foot so as to provide a good protection. The range of the ankle inversion velocity of the normal motions of a foot can be obtained via trials. According to one embodiment, the ankle inversion velocity of any normal motion is between 22.8 to 186.7 degrees per second. Moreover, it is reported in "Biomechanics of supination ankle sprain: A case report of an accidental injury event in the laboratory", Fong D T P, Hong Y, Shima Y, Krosshaug T, Yung P S H, Chan K M, *The American Journal of Sports Medicine*, 37(4):822-827 (2009) that the maximum ankle inversion velocity of a human is 632 degrees per second. Therefore, the threshold for the activation of the stimulating part 130 should be somewhere between 186.7 to 632 degrees per second. In one embodiment, the threshold for the activation of the stimulating part 130 is set in the range between 190-600 degrees per second, such as 200 degrees per second. Optionally, the threshold may be adjustable from 190 to 600 degrees per second according to the needs of the user. For example, the threshold can be set higher when the user is having a high intensity exercise such as running, hiking, playing basketball and the like.

For illustration, individuals with healthy ankles are tested to collect data relating to normal motions of a foot. A gyrometer with a size of 20 mm×18 mm×6 mm used as the sensing part 110 is fixed at the heel of a foot of a user or at the surface of a heel cup of a shoe. The gyrometer is connected to a single printed circuit board (PCB) with a size of 50 mm×25 mm×15 mm to collect the data of motions. The gyrometer monitors the inversion velocity of the foot segment. The sampling frequency of the gyrometer is 500 Hz. The individuals perform five normal motions (i.e. non-sprain motions): walking, running, cutting, jumping-landing and stepping-downstairs. Each motion contributes to 10 trials respectively. These motions are chosen because they are common in human daily activities. The sequences of data collection of different non-sprain motions are random. In walking and running trials, the individuals are requested to walk or run naturally for 5 consecutive strides. The data collection starts from the first stride. In cutting trials, the individuals are requested to perform a single leg cutting by their left or right foot. The individuals run for 5 consecutive strides with full speed before the cut, followed by a 90 degrees cut. In stepping-downstairs trials, data of 3 consecutive strides are collected. In jumping-landing trials, the individuals are requested to perform vertical jumping and landing with both legs to their maximum height. In addition, the individuals are allowed to rest between each trial to ensure that their muscles do not fatigue. Results of the tests are shown in Table 1. It can be seen that the maximum inversion velocity of the motions varies from 22.8 to 186.7 degrees per second. It should be noted that if the conditions of the trials and/or the user are changed, the results of the trials may vary. Therefore, these trials are merely illustrative, and do not limit the embodiments described herein.

TABLE 1

The peak values and the time of peak value of the ankle inversion angle and the ankle inversion velocity during the five motions

|  | Walking | Running | Cutting | Jumping-landing | Stepping-downstairs |
|---|---|---|---|---|---|
| Max ankle inversion (deg) | −8.3 | −13.3 | 8.7 | −2.5 | −36.7 |
| Time of max ankle inversion (s) | 0 | −0.01 | 0.78 | −0.23 | 0.04 |
| Max ankle inversion velocity (deg/s) | −151.2 | −186.7 | −160.0 | −22.8 | −38.3 |
| Time of max ankle inversion velocity (s) | −0.1 | −0.08 | 0.69 | 0.22 | 0.25 |

\* Negative value in maximum ankle inversion and ankle inversion velocity means that the ankle is in an everted position relative to the offset position.
\*\* Negative time means that the time is before the moment of foot strike.

Figure 3:
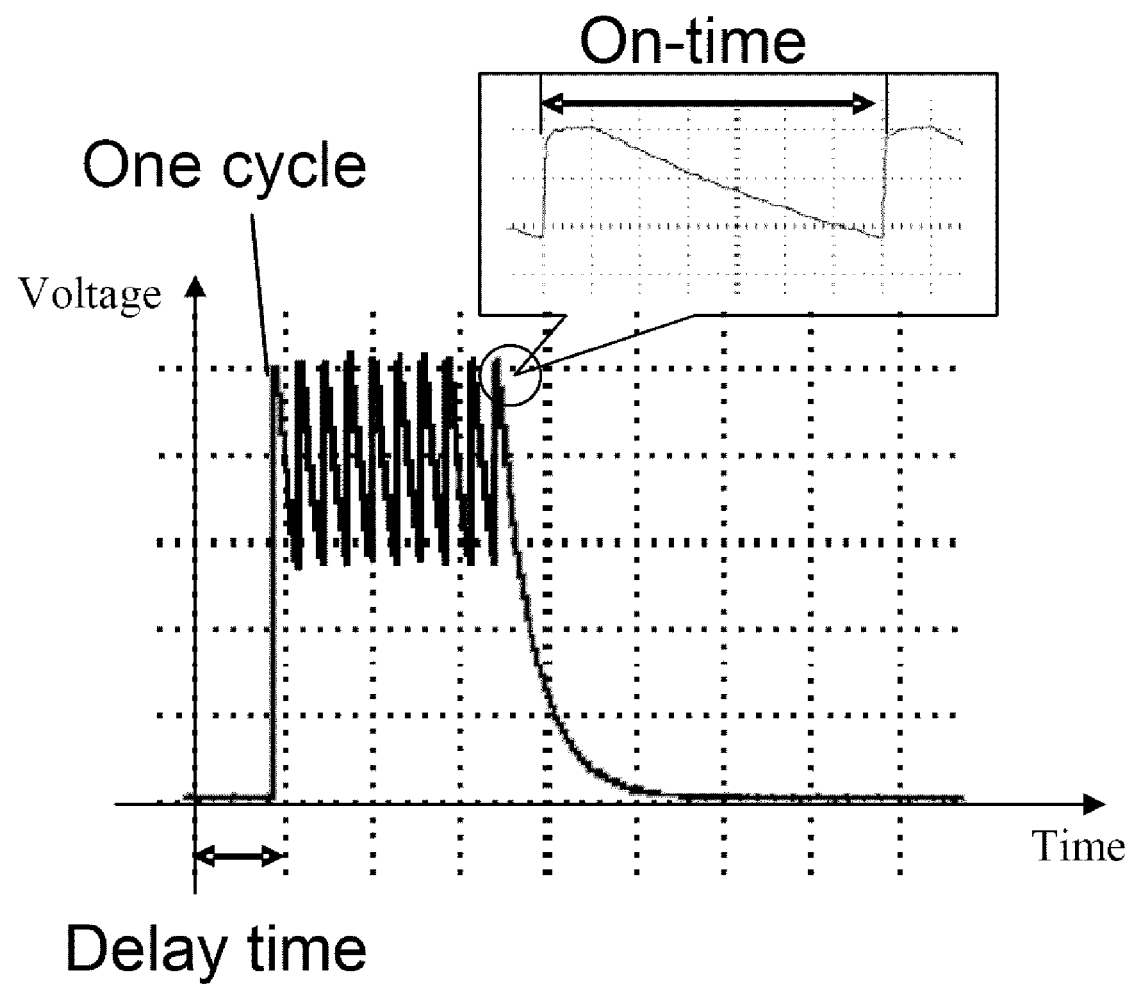
FIG. 3 shows a graph of an exemplary electrical pulse generated by the controlling circuit according to an embodiment of the present invention.
Figure 4:
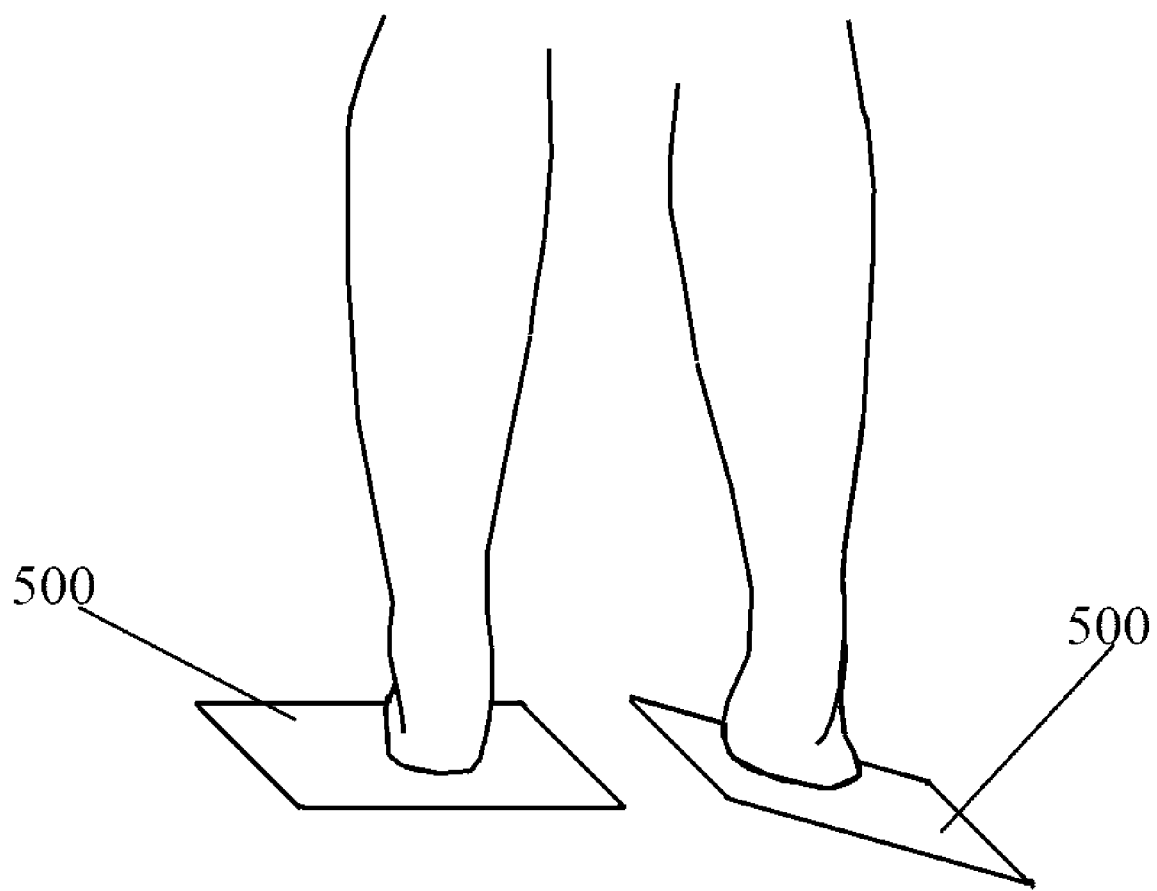
FIG. 4 shows a schematic view of a user's feet standing on the mechanical supination sprain simulator according to an embodiment of the present invention.

According to one embodiment, the electrodes 133 and 134 are attached to the skin surface of the peroneal muscle of a leg of the user. The electric stimulation signal generated by the controlling circuit 132 is an electrical pulse. An exemplary electrical pulse is illustrated in FIG. 3. As shown in FIG. 3, the electrical pulse has a plurality of cycles. The on-time (i.e. the width) of one cycle, the number of the cycles and the delay-time from the start of a sprain injury to the start of the electrical pulse are all adjustable. According to one embodiment, a simple mechanical supination sprain simulator (which is described in "A mechanical supination sprain simulator for studying ankle supination sprain kinematics" Chan Y Y, Fong D T P, Yung P S H, Fung K Y, Chan K M, *Journal of Biomechanics*, 41(11): 2571-2574 (2008)) is used for providing a sudden ankle supination of about 15 or 30 degrees so as to evaluate the effect of different electrical pulses. The two feet of a user stand on two plates 500 in the same horizontal of the mechanical supination sprain simulator, respectively, and then one of the two plates 500 falls to provide a sudden ankle supination of about 15 or 30 degrees, as shown in FIG. 4. The results of trials with different combinations of these parameters are presented in Tables 2(a) and 2(b). The values are averages of several trials.

TABLE 2(a)

Different setting of myoelectric stimulation and the corresponding inversion angle when the platform is dropped to 15 degrees

| Myoelectric stimulation setting | | | Inversion angle of the ankle |
|---|---|---|---|
| Number of cycles | Delay time (ms) | On-time (ms) | when the platform is dropped to 15° |
| No myoelectric stimulation | | | −10.1 |
| 10 | 10 | 5 | −5.5 |
| 10 | 10 | 10 | −4.3 |
| 10 | 15 | 5 | −5.4 |
| 10 | 15 | 10 | −5.1 |
| 10 | 20 | 5 | −5.7 |
| 10 | 20 | 10 | −5.5 |
| 15 | 10 | 5 | −5.9 |
| 15 | 10 | 10 | −5.3 |
| 15 | 15 | 5 | −4.2 |
| 15 | 15 | 10 | −4.5 |
| 15 | 20 | 5 | −6.3 |
| 15 | 20 | 10 | −5.7 |

TABLE 2(b)

Different setting of myoelectric stimulation and the corresponding inversion angle when the platform is dropped to 30 degrees

| Myoelectric stimulation setting | | | Inversion angle of the ankle |
|---|---|---|---|
| Number of cycles | Delay time (ms) | On-time (ms) | when the platform is dropped to 30° |
| No myoelectric stimulation | | | −7.6 |
| 10 | −5.5 | 5 | −5.5 |
| 10 | −4.6 | 10 | −4.6 |
| 10 | −6.4 | 5 | −6.4 |
| 10 | −6.6 | 5 | −6.6 |
| 15 | −6.3 | 10 | −6.3 |

It can be seen from the results that the inversion angle of the ankle with myoelectric stimulation is reduced by various degrees.

A shoe or a brace-like or sock-like ankle protector for preventing the ankle from sprain injuries in sports and outdoor activities is provided, which may comprise the device 100 embedded therein. Those skilled in the art can attach the device 100 to, or embed the device 100 into, a suitable position of the shoe or the protector according to the requirements in practice by sewing, bonding or any other known coupling manner. In one embodiment, an intelligent sprain-free shoe with the device 100 can be beneficial for athletics in sprain prevention.

Furthermore, the device 100 can reduce the cost of treatment in ankle sprain injury. Users also can gain the benefit from a product equipped with the device 100 for preventing sport-related injuries.

Features, integers, characteristics or groups described in conjunction with a particular aspect, embodiment, implementation or example of the invention are to be understood to be applicable to any other aspect, embodiment, implementation or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The present invention is not limited to the embodiments described above. Variations and modification made by those skilled in the art according to the disclosure herein should be within the scope of the present invention.

What is claimed is:

1. A device for preventing an ankle sprain injury, comprising:
    a sensing part configured to sense data related to ankle motion;
    an analyzing part configured to analyze said data to determine whether said motion is a sprain motion, and configured to generate a trigger signal once said data received about a motion exceeds a preset threshold indicative of said sprain motion; and
    a stimulating part configured to stimulate one or more lower limb muscles in response to the trigger signal transmitted from the analyzing part to prevent said sprain motion,
    wherein the data sensed by the sensing part is an ankle inversion velocity.

2. The device of claim 1, wherein the data sensed by the sensing part is transmitted in real-time to the analyzing part in a wired or wireless manner and said sensing part has a sampling frequency in a range of 50 Hz~1,000 Hz.

3. The device of claim 1, wherein said sensing part is attached to an external or internal portion of a shoe or adapted to be attached to a foot.

4. The device of claim 1, wherein the sensing part comprises a tri-axial accelerometer and a gyrometer.

5. The device of claim 1, wherein the sensing part comprises one or more selected from the group consisting of a tri-axial accelerometer, a gyrometer, a goniometer, and a pressure sensor.

6. The device of claim 1, wherein said threshold is adjustable.

7. The device of claim 1, wherein the threshold is between approximately 190 and 600 degrees per second.

8. The device of claim 1, wherein the stimulating part comprises:
    a pair of electrodes configured to be in contact with a lower limb, and
    a circuit configured to deliver an electric stimulation signal applied between the electrodes when the trigger signal is transmitted from the analyzing part.

9. The device of claim 8, wherein the electrodes are adapted to be attached to a skin surface of a peroneal muscle group.

10. The device of claim 9, wherein the electrodes are separated by a distance of 1-3 cm on the skin surface of the peroneal muscle group.

11. The device of claim 8, wherein the electrodes are disposable/replaceable skin-attached discs.

12. The device of claim 8, wherein the electric stimulation signal is an electrical pulse.

13. The device of claim 12, wherein the electrical pulse has a plurality of cycles with an adjustable width.

14. The device of claim 1, wherein said device is incorporated, in whole or in part, into a shoe, sock, brace or other supporting structures.

15. A method for preventing an ankle sprain injury, comprising:
    sensing data related to ankle motion;
    analyzing the data to determine whether said motion is a sprain motion by determining whether said data exceeds a preset threshold indicative of said sprain motion;
    generating a trigger signal if said preset threshold is exceeded by said data; and
    stimulating one or more lower limb muscles in response to said trigger signal to prevent said motion if the motion is a sprain motion,
    wherein the sensed data is an ankle inversion velocity.

16. The method of claim 15, wherein the data is sensed in a real-time manner with a sampling frequency adjustable in a range of 50 Hz~1,000 Hz.

17. The method of claim 15, wherein the sensed data is an ankle inversion velocity.

18. The method of claim 15, wherein said threshold is adjustable.

19. The method of claim 15, wherein the threshold is between approximately 190 and 600 degrees per second.

20. The method of claim 15, wherein the one or more lower limb muscles is a peroneal muscle group.

21. The method of claim 15, wherein the stimulating one or more lower limb muscles comprises stimulating the muscles with an electrical pulse.

22. The method of claim 21, wherein the electrical pulse has a plurality of cycles with an adjustable width.

* * * * *